United States Patent
Prieels

(10) Patent No.: US 9,431,222 B2
(45) Date of Patent: Aug. 30, 2016

(54) DEVICE AND METHOD FOR MEASURING AN ENERGY PARTICLE BEAM

(75) Inventor: Damien Prieels, Court-Saint-Etienne (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 1225 days.

(21) Appl. No.: 13/386,218

(22) PCT Filed: Jul. 23, 2010

(86) PCT No.: PCT/EP2010/060747
§ 371 (c)(1),
(2), (4) Date: Mar. 30, 2012

(87) PCT Pub. No.: WO2011/009953
PCT Pub. Date: Jan. 27, 2011

(65) Prior Publication Data
US 2012/0181442 A1  Jul. 19, 2012

(30) Foreign Application Priority Data
Jul. 24, 2009 (BE) .................. 2009/0453

(51) Int. Cl.
*H01J 47/02* (2006.01)
*G01T 1/185* (2006.01)
*G01N 27/66* (2006.01)

(52) U.S. Cl.
CPC ............. *H01J 47/02* (2013.01); *G01N 27/66* (2013.01); *G01T 1/185* (2013.01)

(58) Field of Classification Search
CPC .......... H01J 47/02; G01T 1/185; G01N 27/66
USPC .................. 250/385.1, 374, 389; 324/464
See application file for complete search history.

(56) References Cited

U.S. PATENT DOCUMENTS

| 2,643,343 A | 6/1953 | Rainwater |
| 3,022,424 A * | 2/1962 | Anton ................. H01J 47/00 250/375 |

(Continued)

FOREIGN PATENT DOCUMENTS

| FR | 1224624 A | 6/1960 |
| GB | 958240 A | 5/1964 |

OTHER PUBLICATIONS

R.F. Laitano et al., "Charge Collection Efficiency in Ionization Chambers Exposed to Electron Beams With High Dose Per Pulse." Physics in Medicine and Biology, vol. 51, 2006, pp. 6419-6436.

(Continued)

*Primary Examiner* — David Porta
*Assistant Examiner* — Blake Riddick
(74) *Attorney, Agent, or Firm* — Fitch, Even, Tabin & Flannery LLP

(57) ABSTRACT

The present invention relates to a dosimetry device for an energy particle beam from a source and including at least two ionization chambers, each of which includes a collector electrode and a polarization electrode, said electrodes in each ionization chamber being separated by a gap including a fluid, an energy beam from a single source passing through said ionization chambers, the device being characterized in that said ionization chambers have different charge collection efficiency factors. Said calculation algorithm for the dose rate deposited by said beam is based on the measurement of an output signal in each ionization chamber of the device and on a □gain□ factor related to a first ionization chamber, said □gain□ factor being theoretically predetermined on the basis of said intrinsic and/or extrinsic parameters of said ionization chambers.

11 Claims, 5 Drawing Sheets

(56) References Cited

U.S. PATENT DOCUMENTS

| | | | | |
|---|---|---|---|---|
| 3,119,036 A * | 1/1964 | Braestrup | ............... | G01T 1/14 250/385.1 |
| 3,287,560 A | 11/1966 | Morgan | | |
| 4,206,355 A * | 6/1980 | Boux | ............... | G01T 1/29 250/374 |
| 4,284,892 A * | 8/1981 | Hulot | ............... | G01T 1/142 250/376 |
| 4,605,858 A * | 8/1986 | Terhune | ............... | G01T 1/026 250/336.1 |
| 4,780,897 A | 10/1988 | McDaniel et al. | | |
| 5,072,123 A * | 12/1991 | Johnsen | ............... | G01T 1/185 250/374 |
| 5,594,252 A * | 1/1997 | Day | ............... | H01J 47/028 250/385.1 |
| 2003/0045916 A1 * | 3/2003 | Anderson | ............... | A61B 5/0064 607/89 |
| 2003/0071222 A1 * | 4/2003 | Harvey | ............... | G01R 29/24 250/397 |
| 2006/0067474 A1 * | 3/2006 | Schmitt | ............... | A61B 6/542 378/102 |
| 2007/0181815 A1 * | 8/2007 | Ebstein | ............... | G01T 1/02 250/370.11 |

OTHER PUBLICATIONS

International Search Report, International Patent Application PCT/EP2010/060747, date of the actual completion Sep. 7, 2010, 6 pages.

* cited by examiner

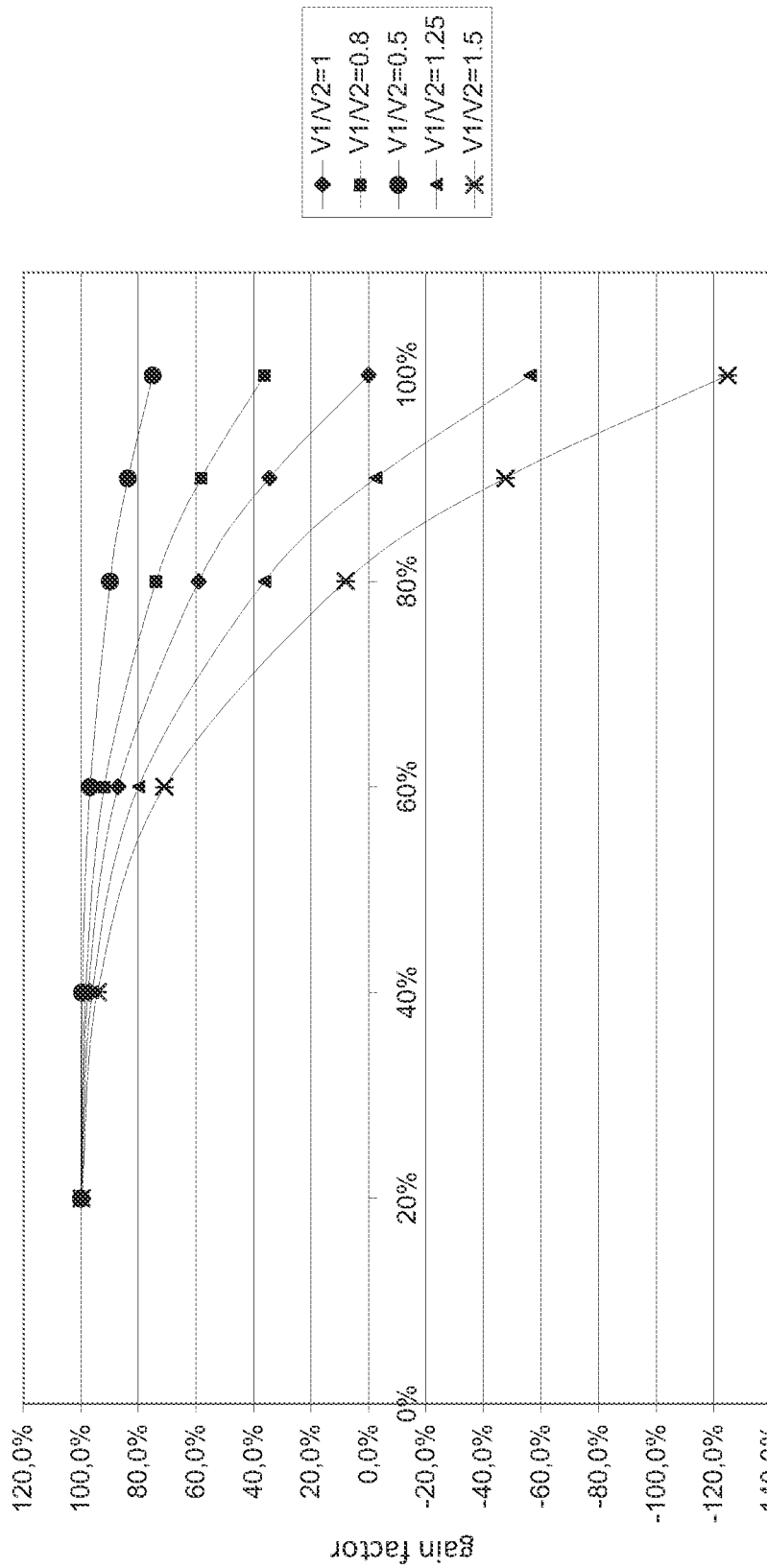

DEVICE AND METHOD FOR MEASURING AN ENERGY PARTICLE BEAM

CROSS REFERENCE TO RELATED APPLICATIONS

This application is a national phase application of International Application No. PCT/EP2010/060747, filed Jul. 23, 2010, designating the United States and claiming priority to Belgium Patent Application No. 2009/0453, filed Jul. 24, 2009, which are incorporated by reference herein in their entirety.

TECHNICAL FIELD

The present invention relates to the field of dosimetry for an energy particle beam. More particularly, the present invention relates to a device comprising several ionization chambers and a method making it possible to measure a charge collection efficiency factor in an ionization chamber.

BACKGROUND OF THE INVENTION

Ionization chambers are standard dosimetry detectors generally used in radiotherapy. An ionization chamber comprises a polarization electrode separated from a collector electrode by a gap or space comprising a fluid of any nature whatsoever (including air).

Several types of ionization chambers are encountered, for example such as so-called cylindrical ionization chambers and ionization chambers comprising parallel plates. Cylindrical ionization chambers comprise a central or axial electrode generally in the form of very fine cylinder, isolated from the second electrode in the form of a hollow cylinder or a hood surrounding said central or axial electrode. Ionization chambers comprising parallel plates have a collector electrode separated from a polarization electrode, said collector and polarization electrodes being planar and parallel to one another.

The fluid comprised in the gap or space separating the collector and polarization electrodes of an ionization chamber used in dosimetry is most often a gas, neutral or not. When an ionizing beam passes through the ionization chamber, there is an ionization of the gas comprised between the electrodes and ion-electron pairs are created. An electric field is generated by applying a potential difference between the two electrodes of the ionization chamber. The presence of the electric field makes it possible to separate these ion-electron pairs and cause them to drift on the electrodes, creating a current at said electrodes that will be detected.

The curve of FIG. 1 is one example of the evolution of the amplitude of the electrical pulse received by the collector electrode as a function of the electric potential difference between the collector electrode and the polarization electrode. This curve can be divided into six zones covering the different gas detector states:

Z1: unsaturated state;
Z2: saturated state;
Z3: proportional state;
Z4: limited proportionality state;
Z5: Geiger-Müller state;
Z6: continuous discharge state.

In zone Z1, called the unsaturated state zone, when the electric field between the two plates is nonexistent, there is a recombination of the ion-electron pairs. By applying an increasing electric potential difference between the two electrodes, the resulting electric field increasingly efficiently separates the ion-electron pairs, and the recombination phenomena are attenuated. The positive and negative charges are driven toward their respective electrodes more and more quickly, as a function of the intensity of the electric field, reducing the ion concentration equilibrium in the gas, and consequently, the number of recombinations. The current measured in the ionization chamber increases with the electric field created in the ionization chamber, reducing the lost charge quantities. When an electric field created between the two electrodes is powerful enough, the recombination effects become negligible and all of the charges created by the ionization process contribute to measuring the current. At that level, the charge collection efficiency is maximal and increasing the potential difference between the two electrodes will no longer make it possible to increase the measured current, since all of the created charges are already collected and their formation speed is constant. One is then in zone Z2, called the saturated state zone, where the dosimetry measurements in the ionization chambers are generally done in radiotherapy. Under these conditions, the measured current is a good indication of the dose deposited by a beam in the volume of the ionization chamber.

Several factors can harm the saturation of an ionization chamber. The most important of these is the recombination phenomenon. This phenomenon can be minimized by adjusting the different parameters of the ionization chamber, such as, for example, the thickness of the gap between the two electrodes, the nature and/or pressure of the gas comprised in that gap, etc. The recombination effects can also depend on the size and/or shape of the beam. The recombination phenomena will also increase proportionally as a function of the intensity of the current of the beam. The current loss percentage due to the recombinations and therefore the error percentage of the current that is measured below the real saturation region increases proportionally with the intensity of the current. For less intense beams, the recombination effect is less decisive. To measure high-intensity beams, a high enough potential difference between the electrodes is required to work under saturation conditions.

For the currents of very high-intensity beams, like those encountered in advanced radiotherapy techniques, the technological usage limit of traditional ionization chambers is reached. The recombination phenomena become very significant and then, a reliable measurement correction method is crucial.

It would be possible to work in the so-called unsaturated state zone Z1 close to the saturated state zone by taking into account the errors due to the recombination, which are significant. In that case, it is necessary to know the saturation levels of the ionization chamber as a function of the beam current. A calibration curve using the intensity of the beam current as a function of the intensity of the collected current can be done by measuring the ionization currents as a function of the beam current, with the aim of knowing the beam current. But for this calibration to remain valid, it is necessary for the other parameters, such as the potential difference applied between the two electrodes, the gap, the pressure inside the ionization chamber, the energy, the size and shape of the beam, to remain constant. Another flaw in this method is that it does not make it possible to differentiate between a variation of the signal due to a beam current and a variation of the signal due to a deregulation of one of the parameters of the ionization chamber. To offset these measurement problems, new dosimetry devices making it possible to measure beam currents in a wide intensity range are necessary.

AIMS OF THE INVENTION

The present invention aims to provide a device and method not having the drawbacks of the devices and methods of the prior art.

In particular, the present invention aims to be able to measure the charge collection efficiency factor in an ionization chamber subject to an energy particle beam.

Another aim of the present invention is to be able to measure the dose or dose rate deposited by a variable energy and/or intensity particle beam under conditions where the charge collection efficiency in an ionization chamber is not maximal, i.e. under conditions where an ionization chamber has significant recombination phenomena.

One additional aim of the present invention is to provide a dosimetry device covering a wide particle beam current intensity range.

BRIEF DESCRIPTION OF THE INVENTION

A first aspect of the present invention relates to a dosimetry device for an energy particle beam coming from a source and comprising at least two ionization chambers each comprising a collector electrode and a polarization electrode, said electrodes of each ionization chamber being separated by a gap or space comprising a fluid with a predetermined pressure and temperature, said ionization chambers being configured to be passed through by an energy particle beam coming from a same source, the device being characterized in that said ionization chambers have different charge collection efficiency factors.

According to the invention, the device comprises an acquisition device connected to a computer performing an algorithm for calculating the dose rate deposited by said particle beam based on:
  measuring an output signal in each considered ionization chamber; and
  a "gain" factor relative to a first ionization chamber, given by the equation $$G = \frac{1 - \left(\frac{i1}{i2}\right)_{norm}}{1 - f_1}$$

where
  G is the "gain" factor relative to the first ionization chamber (IC1), $$\left(\frac{i1}{i2}\right)_{norm}$$

is the ratio of theoretical values of output signals (i1 and i2) in the two considered ionization chambers (IC1 and IC2) normalized by the ratio of their respective amplification factors (R1/R2), each amplification factor depending on said fluid, the width of the gap and the penetration power of the particle beam in said fluid for a considered ionization chamber,
  $f_1$ is the theoretical value of the charge collection efficiency factor in the first ionization chamber (IC1),
said theoretical output signal values (i1, i2) and f1 being calculated as a function of intrinsic and/or extrinsic parameters of said considered chambers (IC1 and IC2), and as a function of the value of the current intensity of the particle beam, said gain factor being independent of the value of said particle beam.

According to one specific embodiment of the invention, said computation algorithm is capable of performing the following steps:
  measuring the output signals (i1 and i2) in the two considered ionization chambers, and establishing a normalized ratio $$\left(\frac{i1}{i2}\right)_{norm}$$

between said output signal values (i1 and i2);
  calculating the charge recombination rate (1−f) and deducing the charge collection efficiency factor (f) in a considered ionization chamber based on the results of the first step of the algorithm and based on the knowledge of the "gain" factor of the considered ionization chamber;
  computing the dose rate deposited by the beam based on a charge collection efficiency factor in the considered ionization chamber.

The charge collection efficiency factor is related to the sensitivity of an ionization chamber and can be defined as a parameter expressing the variation of an output signal of a measuring device as a function of the variation of an input signal. In particular, the output signal is the current measured at the outlet of an ionization chamber.

For an ionization chamber, the sensitivity can depend on:
  the thickness of the gap separating the collector electrode and the polarization electrode,
  the potential difference between the two electrodes,
  the nature of the fluid comprised between the two electrodes,
  the pressure and/or temperature at which the fluid comprised between the two electrodes is found,
  the geometry of the ionization chamber,
  the position of the ionization chamber relative to the position of the source of the energy beam,
  the presence of an energy absorber between the ionization chamber and the source,
the last two factors defining the extrinsic parameters, whereas the first factors define the intrinsic parameters of an ionization chamber.

"Different" refers to a very small variation of at least 0.05%, preferably at least 0.1%, preferably at least 1%. In fact, an efficiency factor difference greater than 0.05% for beam currents from 1 to 100 nA is already sufficient to yield a significant current variation (greater than 1%).

In a first embodiment of the invention, said ionization chambers have a difference in terms of the gap thickness comprised between said collector and polarization electrodes for each ionization chamber.

In a second embodiment, which may or may not be combined with the first embodiment of the invention, said ionization chambers have a difference at the electric fields created between said collector and polarization electrodes for each ionization chamber.

In a third embodiment of the invention combined with one or more of the previous embodiments, said ionization chambers have a difference in terms of the nature of the fluids present in the gap comprised between said collector and polarization electrodes for each ionization chamber.

In a fourth embodiment of the invention combined with one or more of the previous embodiments, said ionization chambers have a difference in terms of the pressure and/or temperature of the fluids present in the gap comprised between said collector and polarization electrodes for each ionization chamber.

In a fifth embodiment of the invention combined with one or more of the previous embodiments, said ionization chambers have a difference in terms of the spatial situation (geometry and/or localization) of the ionization chambers relative to the position of the source, so that the beam field entering each of the ionization chambers differs from one ionization chamber to the other.

In a sixth embodiment of the invention combined with one or more of the previous embodiments, said ionization chambers are separated by one or more energy absorbers, so that the energy beam entering each of the ionization chambers differs from one ionization chamber to the other.

A second aspect of the invention relates to a method for measuring the dose rate deposited by a particle beam, based on the use of the dosimetry device described above.

According to the inventive method, the following steps are carried out, in which:

(i) the device according to any one of the preceding claims is used, for which one chooses the intrinsic and/or extrinsic parameters of each of the considered ionization chambers;

(ii) a "gain" factor is established, given by the equation $$G = \frac{1 - \left(\frac{i1}{i2}\right)_{norm}}{1 - f_1}$$

where

G is the "gain" factor relative to the first ionization chamber (IC1), $\left(\frac{i1}{i2}\right)_{norm}$ is the ratio of theoretical output signal values (i1 and i2) in the two considered ionization chambers (IC1 and IC2) normalized by the ratio of their respective amplification factors (R1/R2), each amplification factor depending on said fluid, the width of the gap and the penetration power of the particle beam in said fluid for a considered ionization chamber, $f_1$ is the theoretical value of the charge collection efficiency factor in the first ionization chamber (IC1), said theoretical output signal values (i1, i2) and f1 being calculated as a function of the intrinsic and/or extrinsic factors of said considered chambers (IC1 and IC2) chosen in the first step of the method and as a function of the value of the current intensity of the particle beam, said gain factor being independent of the value of said current of the particle beam, (iii) the output signal is measured for said two considered ionization chambers;

(iv) said signals are processed using a computer carrying out an algorithm for determining the charge collection efficiency factor of said first chamber, based on the gain factor, followed by the calculation of the dose rate deposited by said beam.

Preferably, said calculation of the dose rate deposited by said particle beam is done using the following steps:

(i) calculating the normalized ratio $$\left(\frac{i1}{i2}\right)_{norm}$$

of the output signals (i1 and i2) measured in the two considered ionization chambers (IC1 and IC2);

(ii) calculating the charge collection efficiency factor f1 in a first ionization chamber based on said gain factor relative to that same ionization chamber and based on the value of the normalized ratio $$\left(\frac{i1}{i2}\right)_{norm}$$

of the output signals (i1 and i2) measured in said two considered ionization chambers (IC1 and IC2);

(iii) calculating the dose rate deposited by said beam based on the measurement of the current in said first ionization chamber and the charge collection efficiency factor relative to said first ionization chamber (IC1).

A third aspect of the invention relates to the use of the measurement method according to the invention to perform a dose rate measurement of an energy particle beam whereof the current intensity is greater than 1 nA.

BRIEF DESCRIPTION OF THE FIGURES

FIG. 6 shows a graph illustrating several curves showing the variation of the gain factor relative to an ionization chamber IC1, as a function of the ratio of the gaps $d_{IC2}/d_{IC1}$ and as a function of the ratio of the potential differences $V_1/V_2$ between the electrodes in each ionization chamber.

DETAILED DESCRIPTION OF THE INVENTION

Figure 1:
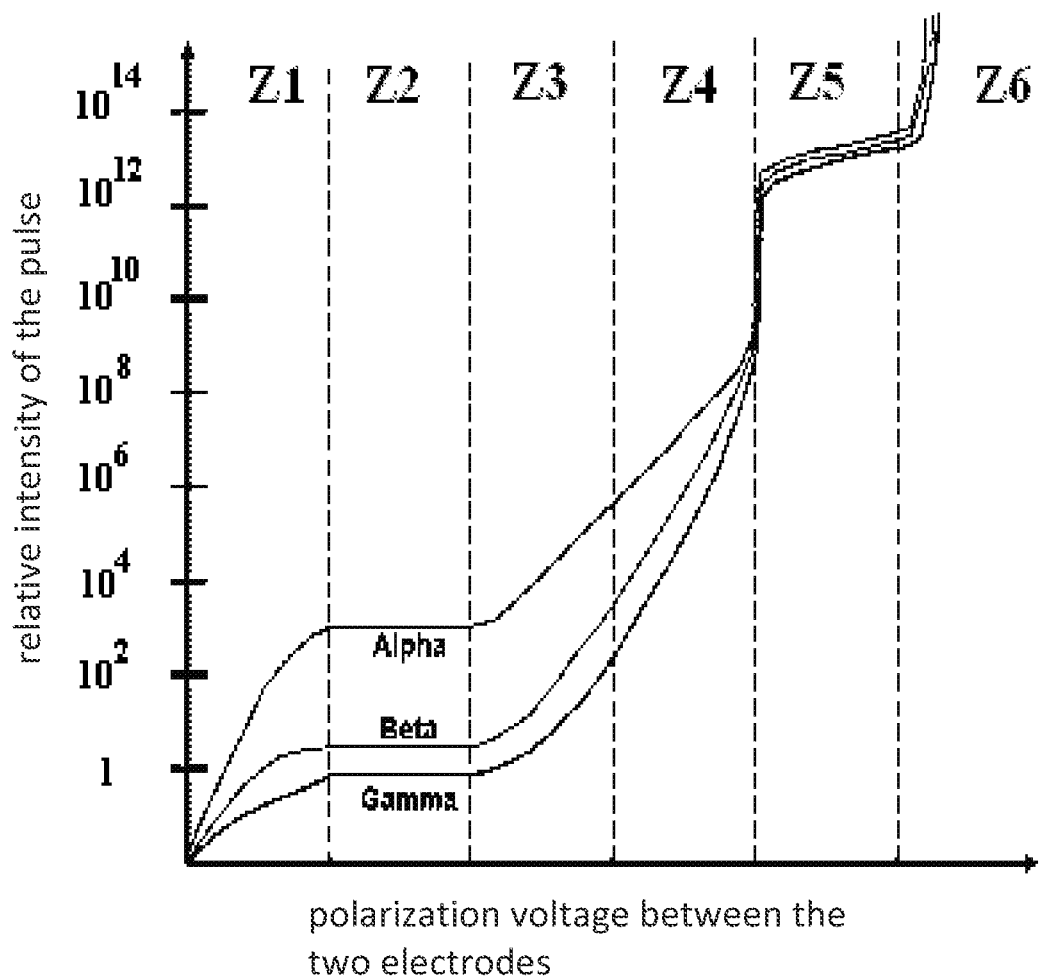
FIG. 1 shows an example of a curve of the evolution of the amplitude of the electric pulse received by the collector electrode as a function of the electric potential difference between the collector electrode and the polarization electrode of a gas detector.

The present invention aims to propose a dosimetry method and device for a particle beam, making it possible to measure the charge collection efficiency in an ionization chamber. The device comprises at least two ionization chambers each comprising a collector electrode and a polarization electrode separated by a gap.

The quantification of the charge collection efficiency in an ionization chamber makes it possible to calculate the dose of the beam, even if the charge collection efficiency in the ionization chamber is not maximal. The dose deposited by a beam, expressed in Gy, is given by formula (1):

$$D = K \cdot \frac{Q}{R \cdot f} \quad (1)$$

with $Q=\int i_{coll}(t)$ and the dose rate deposited by the beam expressed in Gy/s is given by the equivalent formulas (2) or (3):

$$\dot{D} = K \cdot \frac{i_{coll}}{R \cdot f} \quad (2)$$

$$\dot{D} = K \cdot i_{beam} \quad (3)$$

K is a constant of proportionality;
Q is the charge integrated per unit of time;
f is a charge collection efficiency factor in an ionization chamber, expressed in %;
$I_{coll}$ is the current collected in an ionization chamber, expressed in nA and given by equation (4);

$$i_{coll} = f \cdot i_{beam} \cdot R \quad (4)$$

$i_{beam}$ is the intensity of the beam current;
R, the amplification factor of the ionization chamber given by equation (5):

$$R = \frac{10^6 \cdot S \cdot \rho \cdot d}{W} \quad (5)$$

where
$\rho$ is the density of the fluid, generally a gas, comprised in the ionization chamber, expressed in g/cm³;
W is the energy dissipated by the pairs of ions formed, expressed in eV;
d is the thickness of the gap separating the collector electrode and the polarization electrode; and
S is the stopping power of the fluid comprised in the ionization chamber, depending on the energy of the beam and the nature of the fluid, S being expressed in MeV cm²/g.

According to Boag's theory (The dosimetry of ionizing radiation, vol. II, chap. 3, Academic Press, Inc.), the charge collection efficiency factor f of an ionization chamber passed through by a particle beam is given by equation (6):

$$f = \frac{1}{1 + \xi^2} \quad (6)$$

Where $\xi^2$ is given by equation (7):

$$\xi^2 = \left(\frac{\alpha}{6ek_1k_2}\right) \cdot \frac{d^4}{V^2} \cdot Q_{max} \quad (7)$$

where:
α is a recombination coefficient characteristic of the gas comprised in the ionization chamber;
e is the charge of the electron (1.6 10¹⁹C);
$k_1$ and $k_2$ are the positive and negative ion mobilities created in the ionization chamber,
k1 and k2 being expressed in m² s⁻¹ V⁻¹ (in the examples described below, the approximation $k_1=k_2=k$ is done);
V is the potential difference applied between the collector and polarization electrodes, expressed in V; and
$Q_{max}$ is the volumetric ionization density given by equation (8):

$$Q_{max} = \frac{D_{max} \cdot \rho}{W \cdot 10^6} \quad (8)$$

where:
and Dmax is the maximum dose received by the beam in the ionization chamber, given by equation (9):

$$D_{max} = J_{max} \cdot S \quad (9)$$

where
$J_{max}$ is the current density of a particle beam with Gaussian radius σ passing through an ionization chamber, expressed in nA/cm² and given by equation (10):

$$J_{max} = \frac{i_{beam}}{2\pi\sigma^2}. \quad (10)$$

The present invention is based on the use of at least two ionization chambers passed through by a beam coming from a same source, said ionization chambers having different sensitivities. The sensitivity differences are due to one or more differences in the intrinsic or extrinsic parameters between the ionization chambers, such as:
a difference in terms of the thickness of the gap comprised in an ionization chamber;
a difference in terms of the electric field applied in an ionization chamber;
a difference in the nature of the fluid comprised in the gap of an ionization chamber;
a pressure difference of the fluid comprised in the gap from one ionization chamber to the other;
a difference in the energy of the beam entering an ionization chamber;
a difference in the size or shape of the entering beam from one ionization chamber to the other.

These differences between each ionization chamber result in differences in terms of the recombination of ion-electron pairs when a beam passes through each ionization chamber, and therefore different behaviors when one of the ionization chambers operates in the so-called unsaturated state zone Z1, where the recombination of charges is non-negligible.

When the recombination of charges starts to occur there in one of the ionization chambers, owing to the present invention, it is possible to know the charge collection efficiency factor in that ionization chamber by comparing the value of the current measured in that ionization chamber with the value measured in another ionization chamber having at least one difference with regard to the first ionization chamber in terms of the parameters previously described in this paragraph.

Figure 2:
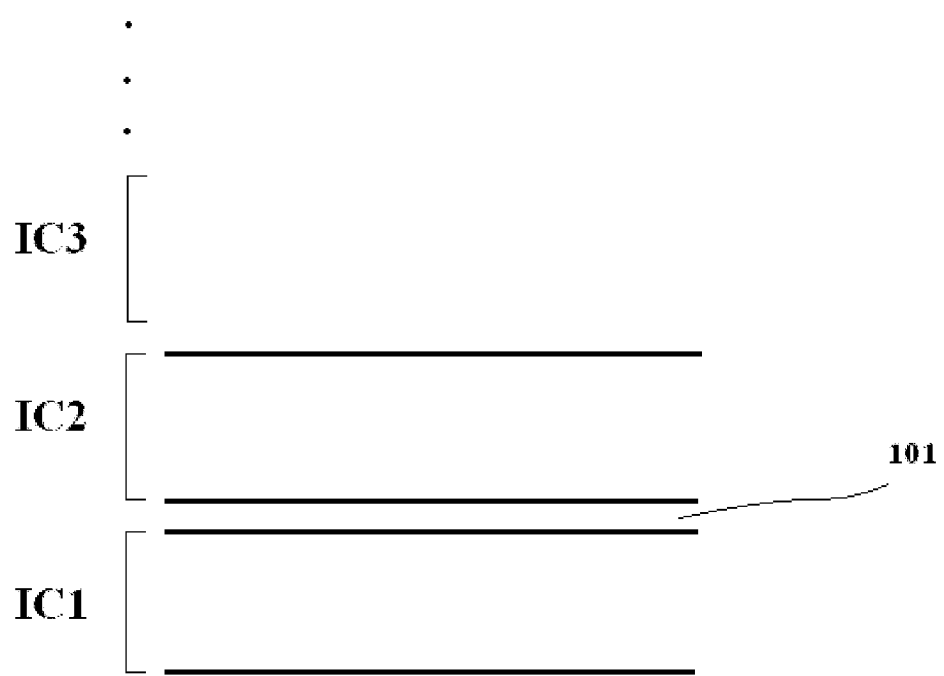
FIG. 2 shows a first embodiment of the invention comprising a device comprising at least two ionization chambers.

FIG. 2 shows one possible embodiment of the present invention comprising at least two planar parallel ionization chambers IC1 and IC2 whereof the plates are separated by an insulating or non-insulating medium 101 and positioned one after the other, preferably normally to the axis of the beam. The same invention can be applied to a device comprising two cylindrical ionization chambers. In the case where the medium 101 is a galvanic insulator, the location of the collector electrodes and polarization electrodes in each of the ionization chambers is not important. In the case where the medium 101 is an electrically conducting medium, it is preferable for the polarization electrode of a first ionization chamber to be situated opposite the polarization electrode of a second ionization chamber.

Figure 3:
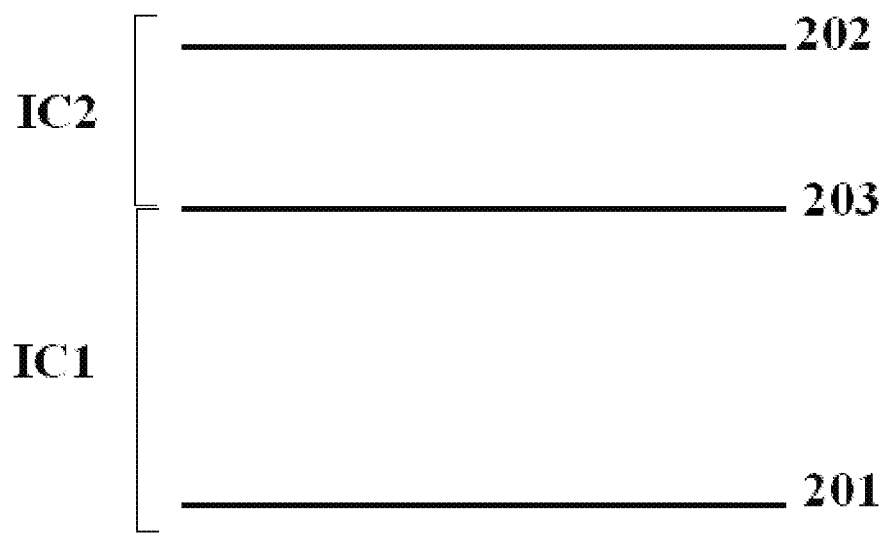
FIG. 3 shows a second embodiment of the invention comprising a device comprising at least two ionization chambers having a shared electrode.

A second embodiment of the present invention is shown in FIG. 3. This involves a device comprising two ionization chambers IC1 and IC1 comprising parallel plates (201, 202, 203), whereof the thickness of the gap between the electrodes of the ionization chamber IC2 is equal to 80% of the thickness of the gap between the electrodes of the ionization chamber IC1. For example, said ionization chamber IC1 can comprise a gap with thickness $d_{IC1}$ equal to 5 mm and said ionization chamber $IC_2$ can comprise a gap with thickness $d_{IC2}$ equal to 4 mm. The two ionization chambers IC1 and IC2 have a shared polarization electrode (203) and are passed through by a proton beam with an energy of 200 MeV and a Gaussian diameter of 10 mm ($\sigma$=5 mm). The different parameters of the ionization chambers IC1 and IC2 are shown in tables 1 and 2, respectively.

TABLE 1

IC 1:

| W | W | 34.7 | eV |
|---|---|---|---|
| Air density | ρ | 0.0013 | g/cm3 |
| Mobility of the ions in the air | k | 1.40E−04 | M2/s/V |
| Recombination coefficient | α | 1.25E−12 | M3/s |
| Charge of the electron | e | 1.60E−19 | C |
| | α/6ekk | 6.64E+13 | V2s/C/m |
| | | 6.643E+11 | V2/A/cm |
| | | 664.32823 | V2/nA/cm |
| Thickness of the gap | $d_{IC1}$ | 0.5 | cm |
| Potential difference | $V_1$ | 1000 | V |
| Electric field | $E_1$ | 2000 | V/cm |
| Migration time | Tcol | 179 | μs |
| Energy of the beam | E | 200 | MeV |
| Stopping power in the air | Sair | 4.00 | MeVcm2/g |
| Amplification factor of the chamber | R1 | 75 | — |
| Gaussian radius of the beam | σ | 0.5 | cm |

TABLE 2

IC 2:

| W | W | 34.7 | eV |
|---|---|---|---|
| Air density | ρ | 0.0013 | g/cm3 |
| Mobility of the ions in the air | k | 1.40E−04 | M2/s/V |
| Recombination coefficient | α | 1.25E−12 | M3/s |
| | e | 1.60E−19 | C |
| | α/6ekk | 6.64E+13 | V2s/C/m |
| | | 6.643E+11 | V2/A/cm |
| | | 664.32823 | V2/nA/cm |
| Thickness of the gap | $d_{IC2}$ | 0.40 | cm |
| Potential difference | $V_2$ | 1000 | V |
| Electric field | $E_2$ | 2500 | V/cm |
| Migration time | Tcol | 114 | μs |
| Energy of the beam | E | 200 | MeV |
| Stopping power in the air | Sair | 4.00 | MeVcm2/g |
| Amplification factor of the chamber | R1 | 60 | — |
| Gaussian radius of the beam | σ | 0.5 | cm |

Table 3 shows, for the ionization chamber $IC_1$, the different values of Jmax, Dmax, Qmax, $\xi^2$, f and $i_{coll}$ calculated based on $i_{beam}$ and equations (4) to (10). In the continuation of the text, for ionization chamber IC1, parameters f and $i_{coll}$ will respectively be called $f_1$ and $i_1$.

TABLE 3

| $i_{beam}$ (nA0) | Jmax (nA/cm2) | Dmax (Gy/sec) | Qmax (nA/cm3) | $\xi^2$ | $f_1$ | $i_1$ (nA) |
|---|---|---|---|---|---|---|
| 0.1 | 0.1 | 0.3 | 9.5 | 0.000 | 99.96% | 7.450 |
| 0.2 | 0.1 | 0.5 | 19.0 | 0.001 | 99.92% | 15 |
| 0.5 | 0.3 | 1.3 | 47.4 | 0.002 | 99.80% | 37 |
| 1 | 0.6 | 2.5 | 94.9 | 0.004 | 99.61% | 74 |
| 2 | 1.3 | 5.1 | 189.8 | 0.008 | 99.22% | 148 |
| 5 | 3.2 | 12.7 | 474.4 | 0.020 | 98.07% | 365 |
| 10 | 6.4 | 25.5 | 948.9 | 0.039 | 96.21% | 717 |
| 20 | 12.7 | 50.9 | 1897.8 | 0.079 | 92.70% | 1382 |
| 50 | 31.8 | 127.3 | 4744.4 | 0.197 | 83.54% | 3113 |
| 100 | 63.7 | 254.6 | 9488.8 | 0.394 | 71.74% | 5346 |
| 200 | 127.3 | 509.3 | 18977.5 | 0.788 | 55.93% | 8336 |
| 500 | 318.3 | 1273.2 | 47443.8 | 1.970 | 33.67% | 12547 |
| 1000 | 636.6 | 2546.5 | 94887.5 | 3.940 | 20.24% | 15087 |
| 2000 | 1273.2 | 5093.0 | 189775.1 | 7.880 | 11.26% | 16786 |
| 5000 | 3183.1 | 12732.4 | 474437.7 | 19.699 | 4.83% | 18002 |
| 10000 | 6366.2 | 25464.8 | 948875.3 | 39.398 | 2.48% | 18448 |

Table 4 shows, for the ionization chamber IC2, the different values of Jmax, Dmax, Qmax, $\xi^2$, f and $i_{coll}$ calculated based on $i_{beam}$ and equations (4) to (10). In the continuation of the text, for ionization chamber IC2, parameters f and $i_{coll}$ will respectively be called $f_2$ and $i_2$.

TABLE 4

| $i_{beam}$ (nA0) | Jmax (nA/cm2) | Dmax (Gy/sec) | Qmax (nA/cm3) | $\xi^2$ | $f_1$ | $i_1$ (nA) |
|---|---|---|---|---|---|---|
| 0.1 | 0.1 | 0.3 | 9.5 | 0.000 | 99.98% | 5.961 |
| 0.2 | 0.1 | 0.5 | 19.0 | 0.000 | 99.97% | 12 |
| 0.5 | 0.3 | 1.3 | 47.4 | 0.001 | 99.92% | 30 |
| 1 | 0.6 | 2.5 | 94.9 | 0.002 | 99.84% | 60 |
| 2 | 1.3 | 5.1 | 189.8 | 0.003 | 99.68% | 119 |
| 5 | 3.2 | 12.7 | 474.4 | 0.008 | 99.20% | 296 |

TABLE 4-continued

| $i_{beam}$ (nA0) | Jmax (nA/cm2) | Dmax (Gy/sec) | Qmax (nA/cm3) | $\xi^2$ | $f_1$ | $i_1$ (nA) |
|---|---|---|---|---|---|---|
| 10 | 6.4 | 25.5 | 948.9 | 0.016 | 98.41% | 587 |
| 20 | 12.7 | 50.9 | 1897.8 | 0.032 | 96.87% | 1155 |
| 50 | 31.8 | 127.3 | 4744.4 | 0.081 | 92.53% | 2758 |
| 100 | 63.7 | 254.6 | 9488.8 | 0.161 | 86.10% | 5134 |
| 200 | 127.3 | 509.3 | 18977.5 | 0.323 | 75.60% | 9015 |
| 500 | 318.3 | 1273.2 | 47443.8 | 0.807 | 55.34% | 16498 |
| 1000 | 636.6 | 2546.5 | 94887.5 | 1.614 | 38.26% | 22810 |
| 2000 | 1273.2 | 5093.0 | 189775.1 | 3.227 | 23.65% | 28206 |
| 5000 | 3183.1 | 12732.4 | 474437.7 | 8.069 | 11.03% | 32871 |
| 10000 | 6366.2 | 25464.8 | 948875.3 | 16.137 | 5.84% | 34789 |

It will be noted that in the case of this first embodiment the invention, as a function of $i_{beam}$, the ionization chamber IC1 has a higher charge recombination rate than the ionization chamber IC2. This effect can be understood using Boag's theory, according to which the probability of charge recombination in an ionization chamber having a gap with thickness d and in which a potential difference V is applied between two electrodes of an ionization chamber, is primarily proportional to the ratio $d^4/V^2$.

Knowing the theoretical values of $f_1$, $f_2$, $i_1$, $i_2$, and having set the gap thicknesses $d_{IC1}$ and $d_{IC2}$, a factor called "gain" factor G is introduced, for example relative to the ionization chamber IC1 and given by two equations (11) and (12):

$$G = \frac{1 - \left(\frac{i1}{i2}\right)_{norm}}{1 - f_1} \quad (11)$$

where $$\left(\frac{i1}{i2}\right)_{norm} = \frac{\left(\frac{i1}{i2}\right)}{\left(\frac{R_{IC1}}{R_{IC2}}\right)} \quad (12)$$

with $R_{IC1}$ and $R_{IC2}$, the amplification factors of the ionization chambers IC1 and IC2, respectively, given by equation (5);
and (1−f1), the charge recombination rate in the ionization chamber IC1.

Table 5 shows, for different values of the ratios i1/i2, the theoretical values of the "gain" factor G of a device comprising two ionization chambers IC1 and IC2 whereof the ratio of the gap thicknesses $d_{IC1}/d_{IC2}$ is 1.25. Again factors constant irrespective of the values of the measured current ratios $i_1/i_2$.

TABLE 5

| $i_{beam}$ | i1/i2 | i1/i2 norm | 1-f1 | $1 - (i_1/i_2)_{norm}$ | Gain = $(1 - (i_1/i_2)_{norm})/(1- f_1)$ |
|---|---|---|---|---|---|
| 0.1 | 1.2497 | 99.98% | 0.04% | 0.02% | 59.04% |
| 0.2 | 1.2494 | 99.95% | 0.08% | 0.05% | 59.04% |
| 0.5 | 1.249 | 99.88% | 0.20% | 0.12% | 59.04% |
| 1 | 1.247 | 99.77% | 0.39% | 0.23% | 59.04% |
| 2 | 1.244 | 99.54% | 0.78% | 0.46% | 59.04% |
| 5 | 1.24 | 98.86% | 1.93% | 1.14% | 59.04% |
| 10 | 1.22 | 97.76% | 3.79% | 2.24% | 59.04% |
| 20 | 1.20 | 95.69% | 7.30% | 4.31% | 59.04% |
| 50 | 1.13 | 90.28% | 16.46% | 9.72% | 59.04% |
| 100 | 1.04 | 83.31% | 28.26% | 16.69% | 59.04% |
| 200 | 0.92 | 73.98% | 44.07% | 26.02% | 59.04% |
| 500 | 0.76 | 60.84% | 66.33% | 39.16% | 59.04% |

TABLE 5-continued

| $i_{beam}$ | i1/i2 | i1/i2 norm | 1-f1 | $1 - (i_1/i_2)_{norm}$ | Gain = $(1 - (i_1/i_2)_{norm})/(1- f_1)$ |
|---|---|---|---|---|---|
| 1000 | 0.66 | 52.91% | 79.76% | 47.09% | 59.04% |
| 2000 | 0.60 | 47.61% | 88.74% | 52.39% | 59.04% |
| 5000 | 0.55 | 43.81% | 95.17% | 56.19% | 59.04% |
| 10000 | 0.53 | 42.42% | 97.52% | 57.58% | 59.04% |

The charge collection efficiency factor f of an ionization chamber, for example the factor $f_1$ of ionization chamber IC1, can be obtained in light of equations (11) and (12), knowing the value of the "gain" factor relative to the ionization chamber IC1, and owing to the measurement of the ratio of the current intensities $i_1$ and $i_2$, measured from the collector electrode (201) of the ionization chamber IC1 and the collector electrode (202) of the ionization chamber IC2, respectively. For example, for a device of this embodiment whereof the polarization electrode (203) is put at a voltage of 1000 V, if the measured value of the ratio $i_1/i_2$ is 1.20, it is possible to calculate the charge collection efficiency factor $f_1$ for the ionization chamber IC1 using equations (11) and (12):

$$1 - f_1 = \frac{1 - \left(\frac{1.20}{\frac{75}{60}}\right)}{0.5904} = 0.073.$$

Hence f1=0.927.

Knowing the measured current ii, the amplification factor $R_1$ of the ionization chamber IC1 and the charge collection efficiency factor of the ionization chamber IC1, it is possible to calculate, based on equation (4), the value of the beam current $i_{beam}$ and thus to know the dose rate deposited by the beam based on equation (3):

$$i_{beam} = \frac{1382 \text{ nA}}{75 \cdot 0.927} \approx 20 \text{ nA} \quad (4)$$

$$D \approx K \cdot 20 \, Gy/s \quad (3)$$

In this case, taking into account the charge collection efficiency factor for the ionization chamber IC1, the true value of the beam current is 20 nA.

Figure 4:
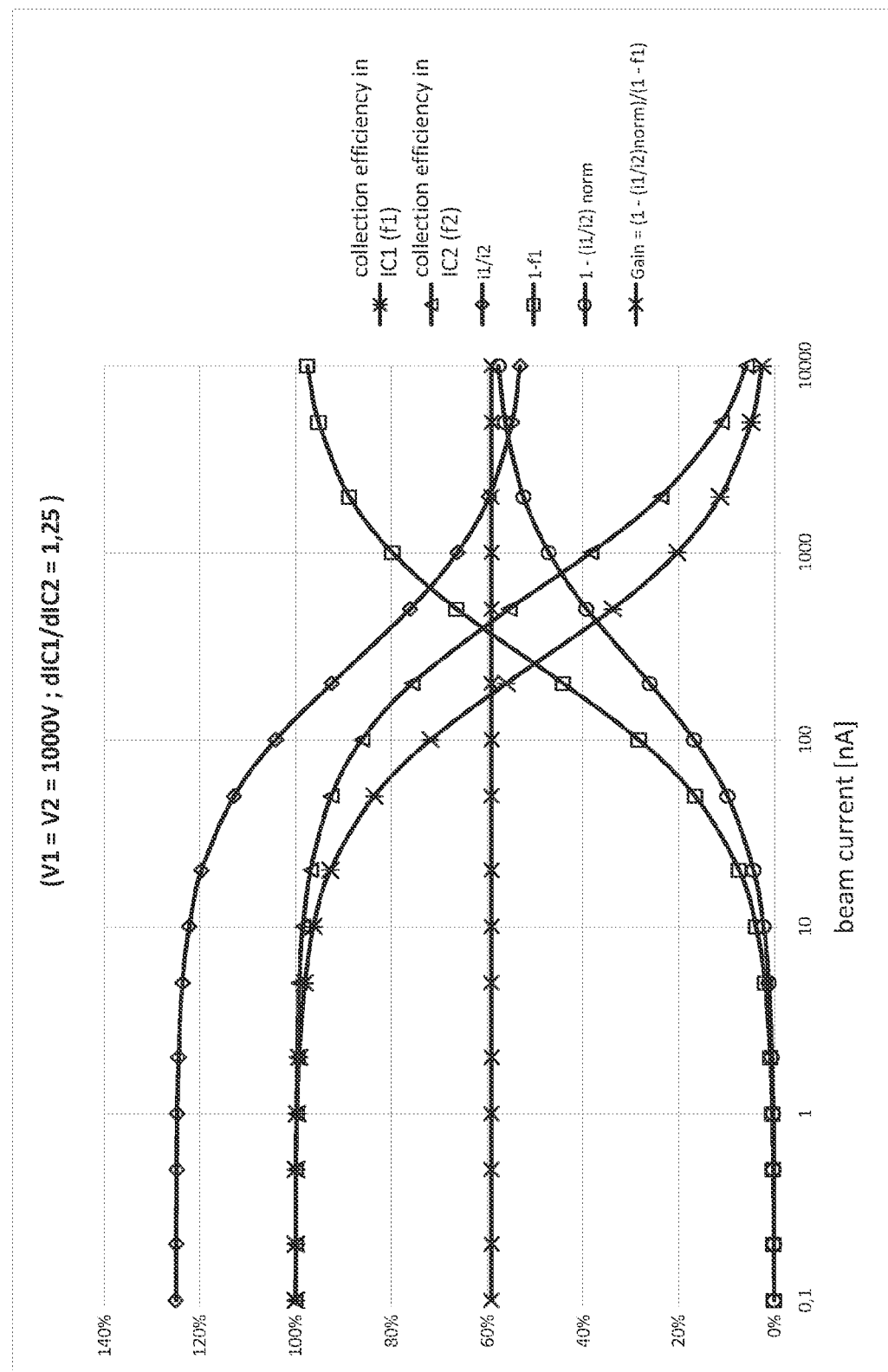
FIG. 4 shows a graph showing the evolution of the charge collection efficiency in two ionization chambers of a device according to the present invention, the ionization chambers being passed through by a same proton beam with a Gaussian radius a equal to 5 mm and energy of 200 MeV, as well as the evolution of the ratio of the currents measured in the two ionization chambers, as a function of the beam current, said device comprising two ionization chambers comprising a different gap.

The situation is shown in the graph of FIG. 4, showing different curves:
the charge collection efficiency factor in the ionization chamber IC1, shown by curve $f_1$,
the charge collection efficiency factor in the ionization chamber IC2, shown by curve $f_2$,
the ratio of the measured currents $i_1/i_2$
the charge recombination rate (1−$f_1$) of the ionization chamber IC1,
the curve $$1 - \left(\frac{i1}{i2}\right)_{norm},$$

the "gain" factor G given by equation (11).
The advantage of using a device comprising two ionization chambers only having differences in terms of the gap thicknesses comprised in each ionization chamber, and whereof the polarization electrode is shared by the two ionization chambers, is that the "gain" factor only depends on the geometry of the chamber. For example, if one changes the electric potential of the polarization electrode shared by the two ionization chambers, although the value of the measured currents and the ratio of those measured currents $i_1/i_2$ will vary, the gain factor remains constant and the variation of the ratio $i_1/i_2$ is counterbalanced by the variation of the charge collection efficiency factor in each ionization chamber. For example, if the polarization electrode is placed at a potential of 2000 V, for a beam current of 20 nA, the value of the measured ratio of the ratio $i_1/i_2$ will be 1.236 with a charge collection factor f1 equal to 0.981. The measured value of $i_1$ being equal to 1462 nA, $i_{beam}$ is 1462/(75·0.981)≈20 nA and the dose rate deposited by the beam is ≈K.20 as in the case of first example, where the voltage of the polarization electrode was 1000 V. The same reasoning applies for an identical variation in both ionization chambers of:

the pressure on the fluid comprised in each ionization chamber;
the nature of the fluid comprised in each ionization chamber;
the size of the beam;
the energy of the beam.

In other words, in calculating the dose rate deposited by the beam, if there is, identically in each ionization chamber, a variation of the electric field, the pressure, the nature of the fluid, or the size of the beam, the variation of the ratio of the measured currents from the collector electrodes of the ionization chambers is counterbalanced by the variation of the charge collection efficiency factor. The device according to the present invention will always provide an accurate measurement of the dose of the beam, provided that these variations are known by one skilled in the art to be able to be applied to the proper operation of an ionization chamber.

Different "gain" factors can be obtained depending on the chosen gap thicknesses. In the example described above, with a beam of 200 MeV, with a Gaussian distribution of 5 mm (1σ) and with a ratio of the gap thicknesses $d_{IC2}/d_{IC1}$ equal to 80%, one obtains a "gain" factor of 59%. It is preferable for the gain factor to be high so as to obtain significant current differences between two ionization chambers and precisely evaluate the charge collection efficiency factor in one of the ionization chambers, and therefore to be able to obtain the dose rate deposited by the beam. As previously discussed, in the present embodiment of the invention, the "gain" factor only depends on the ratio between the thicknesses of the gaps.

FIG. 6 illustrates a curve showing the evolution of the "gain" factor relative to an ionization chamber IC1, for a device comprising two ionization chambers inside which the potential differences in the two ionization chambers are identical ($V_1=V_2$), as a function of the ratio between the thicknesses of the gaps $d_{IC2}/d_{IC1}$. The more this ratio decreases, the higher the gain is and the more it tends toward 100%. It is therefore advantageous to work with a device comprising at least two ionization chambers having different gap thicknesses. One skilled in the art will recognize that a risk of producing electric arcs will exist for an ionization chamber having too small a gap, and that such an ionization chamber comprised in the device according to the present invention will therefore be inappropriate. Likewise, too high a gap will result in increasing the risk of charge recombinations.

As shown in table 6, varying the ratio ($i1/i2$) norm in relation to its value corresponding to a beam current value tending toward 0 becomes significant (i.e. greater than 1%) in the beam current value bracket comprised between 1 and 100 nA for charge collection efficiency factor differences greater than 0.05% for two chambers passed through by a beam current greater than 1 nA.

TABLE 6

| $i_{beam}$ | $d_{IC1}$ = 0.5 cm $f_1$ | $d_{IC1}$ = 0.48 cm $f_2$ | Δf | $(i_1/i_2)$norm | variation of $(i_1/i_2)_{norm}$ relative to its value for $i_{beam}$ = 0.1 |
|---|---|---|---|---|---|
| 0.1 | 99.96% | 99.97% | 0.01% | 99.99% | 0.00% |
| 0.2 | 99.92% | 99.93% | 0.01% | 99.99% | 0.01% |
| 0.5 | 99.80% | 99.83% | 0.03% | 99.97% | 0.02% |
| 1 | 99.61% | 99.67% | 0.06% | 99.94% | 0.05% |
| 2 | 99.22% | 99.34% | 0.12% | 99.88% | 0.11% |
| 5 | 98.07% | 98.35% | 0.29% | 99.71% | 0.29% |
| 10 | 96.21% | 96.76% | 0.57% | 99.43% | 0.57% |
| 20 | 92.70% | 93.73% | 1.11% | 98.90% | 1.09% |
| 50 | 83.54% | 85.67% | 2.54% | 97.52% | 2.47% |
| 100 | 71.74% | 74.93% | 4.45% | 95.74% | 4.25% |
| 200 | 55.93% | 59.91% | 7.11% | 93.36% | 6.63% |
| 500 | 33.67% | 37.41% | 11.10% | 90.01% | 9.99% |
| 1000 | 20.24% | 23.01% | 13.66% | 87.98% | 12.01% |
| 2000 | 11.26% | 13.00% | 15.43% | 86.63% | 13.36% |
| 5000 | 4.83% | 5.64% | 16.74% | 85.66% | 14.33% |
| 10000 | 2.48% | 2.90% | 17.22% | 85.31% | 14.69% |

Another embodiment of the present invention is a device comprising two ionization chambers whereof a parameter other than the thickness of the gap between the two collector and polarization electrodes is different from one ionization chamber to the other. For example, it is possible to apply different potential differences between the electrodes of each ionization chamber, and to measure and compare the current in said ionization chambers so as to have access to the charge collection efficiency relative to an ionization chamber and the dose rate deposited by the beam.

Figure 5:
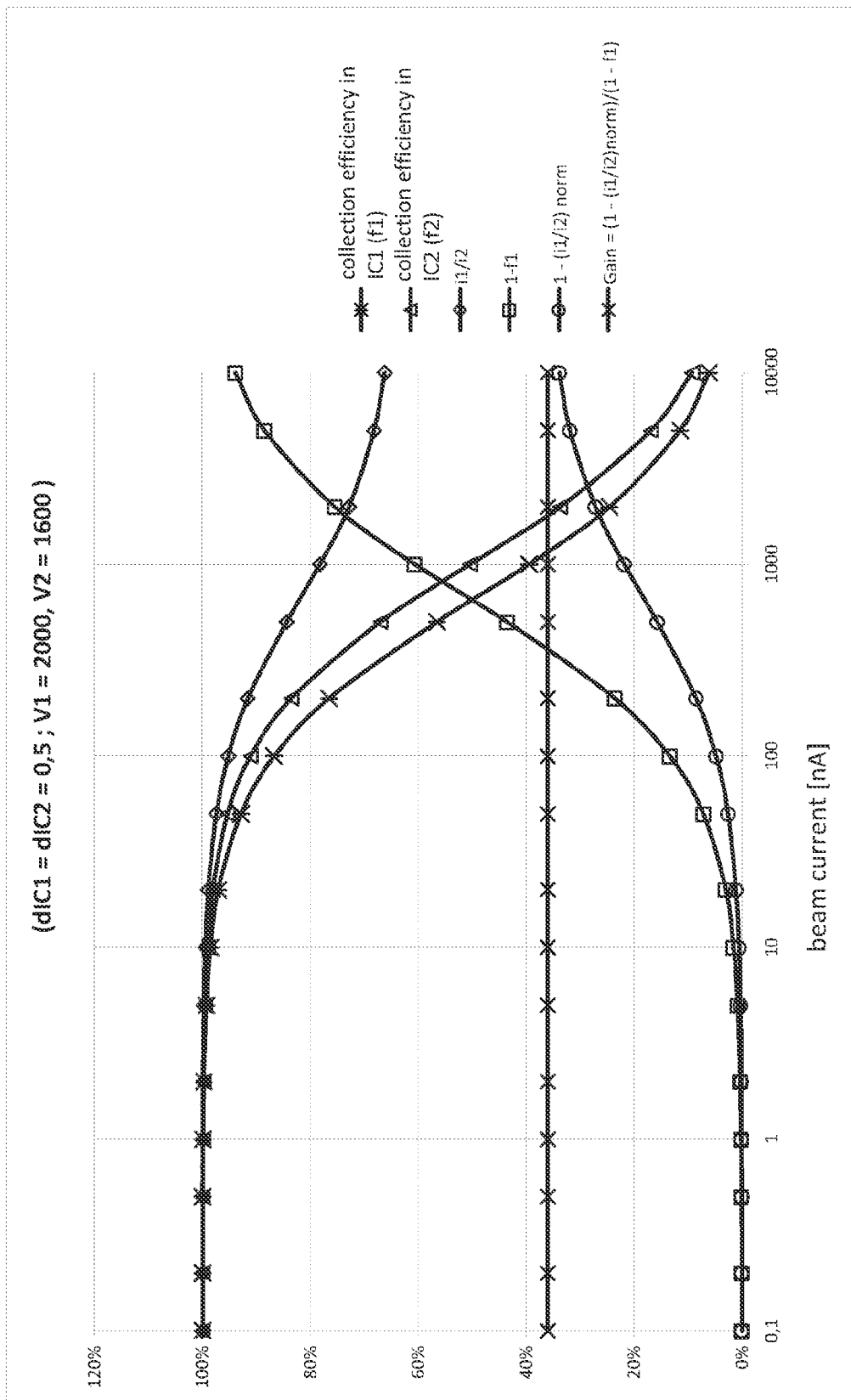
FIG. 5 shows a graph showing the evolution of the charge collection efficiency in two ionization chambers of a device according to the present invention, as a function of the beam current, said ionization chambers comprising an identical gap inside which the electric field created is different from one ionization chamber to the other, the ionization chambers being passed through by a same proton beam with a Gaussian radius a equal to 5 mm and energy of 200 MeV. The graph of FIG. 5 also shows the evolution of the ratio of the currents measured in the two ionization chambers as a function of the beam current.

One example of a device according to this embodiment comprises two ionization chambers with identical gaps, the electrodes of the first ionization chamber IC1 subject to a potential difference $V_1$ of 1600 Volts while the electrodes of the second ionization chamber are subject to a potential difference $V_2$ of 2000 Volts. The two ionization chambers for example have a gap 5 mm thick, may or may not have a shared electrode, and are passed through by a proton beam with an energy of 200 MeV, a Gaussian diameter of 10 mm (σ=5 mm). A current intensity $i_1$ is measured in the ionization chamber IC1 and a current intensity $i_2$ is measured in the ionization chamber IC2. In the present example, as a function of the growth of the intensity of the beam current, the first chamber that starts to have charge recombination phenomena is chamber IC1. In fact, according to Boag's theory, the charge recombination probability in an ionization chamber having a gap with thickness d and subject to an electric potential V is proportional to the ratio $d^4/V^2$. It is possible to calculate a "gain" factor relative to the ionization chamber IC1 of 36% in the case of the present example, the "gain" factor only being dependent on the potential differences between the electrodes of each ionization chamber, inasmuch as the other parameters such as the gap, the pressure, and the nature of the fluid in that gap are constant from one ionization chamber to the other. This situation is shown in the graph of FIG. 5.

In the same way as in the previous embodiment of the invention, the gain factor relative to an ionization chamber being set, the measured ratio of the currents $i_1/i_2$ makes it possible to deduce the charge collection efficiency factor in that same ionization chamber and from there, the deposited dose in that same ionization chamber.

In this present embodiment of the invention, the "gain" factor being lower than that obtained in the case of the previous embodiment, the variation of the ratio of the measured currents $i_1/i_2$ is smaller and as a result, the sensitivity of the measurement of the dose rate deposited by the beam is decreased. Furthermore, the "gain" factor here only depending on potential differences applied in each ionization chamber, a means for monitoring the electric field applied in each ionization chamber is therefore necessary.

Another embodiment of the invention is a device comprising two ionization chambers, each comprising a unique gap thickness and in which the potential differences between the electrodes are different, so as to obtain an optimal "gain" factor. The graph of FIG. 6 shows several curves showing the variation of the gain factor relative to an ionization chamber IC1 as a function of the ratio of the gaps $d_{IC2}/d_{IC1}$ and as a function of the ratio of the potential differences $V_1/V_2$ between the electrodes of each ionization chamber IC1 and IC2. One can see that the gain factor is advantageously higher when the ratio $d_{IC1}/d_{IC2}$ is greater than 1 and that simultaneously, the ratio of the potential differences $V_1/V_2$ between the electrodes of each ionization chamber is less than 1. One skilled in the art will nevertheless recognize the extreme gap values $d_{IC1}$ and $d_{IC2}$ as well as the extreme potential difference values $V_1$ and $V_2$ between the electrodes of each ionization chamber IC1 and IC2, beyond which arc phenomena or precision problems in measuring the beam current occur. It is also possible to work under the opposite conditions, with ratios $d_{IC1}/d_{IC2}$ smaller than 1 and values $V_1/V_2$ greater than 1, in which case the ratio i1/i2 is greater than the ratio $R_1/R_2$ and the "gain" factor assumes values going from 0 to $-\infty$, which, in the absolute, changes nothing about the precision of the determination of the charge collection efficiency and the dose rate deposited by the beam.

Another embodiment of the invention is a device comprising at least two ionization chambers, each comprising a gap, which may or may not be identical, in which the potential differences between electrodes may or may not be different and each comprising a fluid whereof the nature differs from one ionization chamber to the other, such as, for example:

a gas in one ionization chamber and a liquid in another ionization chamber;
a first gas in an ionization chamber and a second gas of a different nature in another ionization chamber;
fluids subject to different pressures.

The parameters S (stopping power of the fluid), $\rho$ (density of the fluid) and W (energy dissipated by the formed pairs of ions) of equation (9) depend both on the nature of the fluid and the pressure at which the fluid is found. Similarly to the situations previously described, it is possible to calculate a gain factor based on the parameters S, $\rho$, and W for each ionization chamber. One can therefore choose a fluid $M_1$ with pressure $P_1$ having parameters $S_1$, $\rho_1$ and $W_1$, and a fluid $M_2$ with pressure $P_2$ having parameters $S_2$, $\rho_2$ and $W_2$, M1 being able to be different from or equal to M2, P1 being able to be different from or equal to P2, and calculating a gain factor using formulas (3) to (11). The fluids M1 and M2 will be comprised in one of the ionization chambers, so as to obtain a high "gain" factor. Similarly to the embodiments previously described, knowing the "gain" factor, the ratio $R_1/R_2$, and having measured the ratio of the currents in each ionization chamber, one determines the charge collection efficiency factor relative to an ionization chamber and deduces therefrom, using formula (2), the dose rate deposited by the beam. If the fluids present in the gaps are at different pressures from one ionization chamber to the other, a means for monitoring the pressure is necessary.

Another embodiment of the invention is a device comprising two ionization chambers and an energy absorber whereof the stopping power S is known, the energy absorber being placed between the two ionization chambers, so as to obtain a different energy of the beam from one ionization chamber to the other, and therefore a different measured current.

Another possible embodiment of the invention is a device whereof at least two ionization chambers are spaced apart from one another so as to have a different beam size or shape entering each ionization chamber, and therefore differences in terms of the measured current density as well as the charge collection efficiency level from one ionization chamber to the other. This involves being able to know the widening of the beam at the same time to calculate the gain factor, which can for example be done using an ionization chamber made up of pixels. Nevertheless, in this embodiment, the current differences measured between two ionization chambers are less significant than in the previous embodiments.

A device combining one or more differences between each ionization chamber as discussed in the embodiments previously described, or also other differences known by those skilled in the art, can be done so as to obtain an optimal gain factor, preferably as high as possible, and a significant difference in the measured current between each ionization chamber, thereby making it possible to know the charge collection efficiency factor of an ionization chamber and to determine the dose rate deposited by a beam, preferably as precisely as possible.

The embodiments of the present invention have been described for uses for monitoring a proton beam dose, but the present invention can also be applied to any other type of ionizing beam.

Lastly, the device according to the present invention is connected to an acquisition device sending the information to a system carrying out an algorithm, the steps of which are as follows:

comparing the differences in the current or currents integrated into two ionization chambers of the device, more particularly the ratio of the measured currents $i_1/i_2$;
calculating the charge recombination rate (1−f), and from there, the charge collection efficiency factor f in a considered ionization chamber based on the results of the first step of the algorithm and based on a "gain" factor of the considered ionization chamber, the "gain" factor being set based on intrinsic parameters (thickness of the gap, potential differences between electrodes of each ionization chamber, nature and pressure of the fluid comprised in the ionization chambers) and extrinsic parameters (size of the beam entering the ionization chambers) of the ionization chambers of the device;
calculating the dose rate deposited by the beam based on the charge collection efficiency factor in the considered ionization chamber.

The device according to the present invention has the advantage of being able to evaluate the charge recombination rate and the charge collection efficiency factor in an ionization chamber, and thus being able to know the dose rate deposited by a beam under conditions where the intensity of the beam is such that a traditional ionization chamber has recombination phenomena. Being able to access the charge collection efficiency factor directly enables precise monitoring of the dose rate deposited by energy-intense beams, i.e. under conditions that would not be measurable with traditional ionization chambers. The device according to the present invention is therefore capable of using ionization chambers over a very wide range of beam currents relative to the known techniques of the prior art.

The invention claimed is:

1. A dosimetry device for an energy particle beam coming from a source and comprising at least first and second ionization chambers each comprising a collector electrode and a polarization electrode, said electrodes of each ionization chamber being separated by a gap or space comprising a fluid, said ionization chambers being configured to be passed through by an energy particle beam coming from a same source, wherein the ionization chambers have different charge collection efficiency factors, and the device comprises an acquisition device connected to a computer configured to perform an algorithm for calculating the dose rate deposited by said particle beam based on:
   measuring an output signal in each considered ionization chamber; and
   a gain factor relative to a first ionization chamber, given by the equation $$G = \frac{1 - \left(\frac{i1}{i2}\right)_{norm}}{1 - f_1}$$

where
G is the gain factor relative to the first ionization chamber, $\left(\frac{i1}{i2}\right)_{norm}$ is the ratio of theoretical values of output signals (i1 and i2) in the two considered ionization chambers normalized by the ratio of their respective amplification factors (R1/R2), each amplification factor depending on said fluid, the width of the gap and the penetration power of the particle beam in said fluid for a considered ionization chamber,
$f_1$ is the theoretical value of the charge collection efficiency factor in the first ionization chamber,
said theoretical output signal values (i1, i2) and f1 being calculated as a function of intrinsic and/or extrinsic parameters of said considered chambers, and as a function of one or more pre-defined values of the current intensity of the particle beam, said gain factor G being independent of the value of said particle beam current intensity.

2. The device according to claim 1, wherein said computation algorithm is configured to perform the following steps:
   measuring the output signals (i1 and i2) in the two considered ionization chambers, and establishing a normalized ratio $\left(\frac{i1}{i2}\right)_{norm}$ between said output signal values (i1 and i2);

calculating the charge recombination rate (1−f) and deducing the charge collection efficiency factor (f) in a considered ionization chamber based on the results of the first step of the algorithm and based on the knowledge of the gain factor of the considered ionization chamber; and
   computing the dose rate deposited by the beam based on a charge collection efficiency factor in the considered ionization chamber.

3. The device according to claim 1, wherein said considered ionization chambers have a difference in terms of the gap thicknesses comprised between said collector and polarization electrodes, imparting a charge collection efficiency factor difference.

4. The device according to claim 1, wherein said considered ionization chambers have a difference at the electric fields created between said collector and polarization electrodes, imparting a charge collection efficiency factor difference.

5. The device according to claim 1, wherein said considered ionization chambers have a difference in terms of the nature of the fluids present in the gap comprised between said collector and polarization electrodes for each ionization chamber, imparting a charge collection efficiency factor difference.

6. The device according to claim 1, wherein said considered ionization chambers have a difference in terms of the pressure and/or temperature of the fluids present in the gap comprised between said collector and polarization electrodes for each ionization chamber, imparting a charge collection efficiency factor difference.

7. The device according to claim 1, wherein said considered ionization chambers have a difference in terms of their geometry and/or localization relative to the position of the source, so that the beam field entering each of the ionization chambers differs from one ionization chamber to the other, imparting a charge collection efficiency factor difference.

8. The device according to claim 1, wherein said considered ionization chambers are separated by one or more energy absorbers, so that the energy beam entering each of the ionization chambers differs from one ionization chamber to the other, imparting a charge collection efficiency factor difference.

9. A method for measuring the dose rate deposited by a particle beam coming from a source, the method comprising:
   (i) utilizing the device according to claim 1, for which one chooses the intrinsic and/or extrinsic parameters of each of the considered ionization chambers;
   (ii) establishing a gain factor, given by the equation $$G = \frac{1 - \left(\frac{i1}{i2}\right)_{norm}}{1 - f_1}$$

where
G is the gain factor relative to the first ionization chamber, $\left(\frac{i1}{i2}\right)_{norm}$ is the ratio of theoretical output signal values (i1 and i2) in the two considered ionization chambers normalized by the ratio of their respective amplification factors (R1/R2), each amplification factor depending on said fluid, the width of the gap and the penetration power of the particle beam in said fluid for a considered ionization chamber, and f1 is the theoretical value of the charge collection efficiency factor in the first ionization chamber, said theoretical output signal values (i1, i2) and f1 being calculated as a function of the intrinsic and/or extrinsic factors of said considered chambers chosen in the first step of the method and as a function of one or more pre-defined values of the current intensity of the particle beam, said gain factor G being independent of the value of said particle beam current intensity, (iii) measuring the output signal for said two considered ionization chambers; and (iv) processing said signals using a computer configured to carry out an algorithm for determining the charge collection efficiency factor of said first chamber, based on the gain factor, followed by calculating the dose rate deposited by said beam.

10. The method for measuring the dose rate deposited by an energy particle beam according to claim 9, wherein said calculation of the dose rate deposited by said particle beam is done using the following steps:

(i) calculating the normalized ratio $$\left(\frac{i1}{i2}\right)_{norm}$$

of the output signals (i1 and i2) measured in the two considered ionization chambers;

(ii) calculating the charge collection efficiency factor f1 in a first ionization chamber based on said gain factor relative to that same ionization chamber and based on the value of the normalized ratio $$\left(\frac{i1}{i2}\right)_{norm}$$

of the output signals (i1 and i2) measured in said two considered ionization chambers; and (iii) calculating the dose rate deposited by said beam based on the measurement of the current in said first ionization chamber and the charge collection efficiency factor relative to said first ionization chamber.

11. A use of measuring method according to claim 9 to perform a dose rate measurement of an energy particle beam whereof the current intensity is greater than 1 nA.

* * * * *